United States Patent [19]

Lever et al.

[11] Patent Number: 5,747,307
[45] Date of Patent: May 5, 1998

[54] MASON-PFIZER MONKEY RETROVIRAL PACKAGING DEFECTIVE VECTORS

[75] Inventors: Andrew Michael Lindsay Lever, Cambridge, England; Eric Hunter, Birmingham, Ala.

[73] Assignee: Syngenix Limited, Cambridge, England

[21] Appl. No.: 295,737

[22] PCT Filed: Mar. 1, 1993

[86] PCT No.: PCT/GB93/00417

§ 371 Date: Aug. 26, 1994

§ 102(e) Date: Aug. 26, 1994

[87] PCT Pub. No.: WO93/17118

PCT Pub. Date: Sep. 2, 1993

[30] Foreign Application Priority Data

Feb. 28, 1992 [GB] United Kingdom .................. 9204350
Apr. 16, 1992 [GB] United Kingdom .................. 9208489
Sep. 2, 1992 [GB] United Kingdom .................. 9219935

[51] Int. Cl.$^6$ .............. C12N 15/00; C12N 15/63; C12N 5/06
[52] U.S. Cl. ............... 435/172.3; 435/320.1; 435/325
[58] Field of Search .................. 435/320.1, 172.3, 435/240.1, 325

[56] References Cited

FOREIGN PATENT DOCUMENTS 9119798  12/1991  WIPO.

OTHER PUBLICATIONS

Francki, R.I.B. et al. (1992) "Classification and Nomenclature of Viruses" Fifth Report of the International Committee on Taxonomy of Viruses, Archives of Virology Supplementum 2, pp. 293, 295, 297, 298.

Vile, Richard G. et al. (1992) "Identification of a Generalised Packaging Sequence for D–Type Retroviruses and Generation of a D–Type Retroviral Vector" Virology 189:786–791.

Primary Examiner—Douglas W. Robinson
Assistant Examiner—Thanda Wai
Attorney, Agent, or Firm—Saliwanchik, Lloyd & Saliwanchik

[57] ABSTRACT

Novel vectors are capable of producing MPMV (Mason-Pfizer Monkey Virus) proteins but not of packaging MPMV RNA, and the information about the packaging signal in MPMV and HIV can be used to create MPMV and HIV vectors that are capable of transferring foreign genes, e.g. for use in gene therapy.

12 Claims, 5 Drawing Sheets

FIG. 5A  pSVC21
FIG. 5B  pHXBΔP1
FIG. 5C  pHXBΔP2
FIG. 5D  pHXBΔP1ΔLTR
FIG. 5E  pHXBΔP1Δenv
         +
         pLenv

MASON-PFIZER MONKEY RETROVIRAL PACKAGING DEFECTIVE VECTORS

This application is a 371 of PCT/GB93/00417, filed on Mar. 1, 1993.

FIELD OF THE INVENTION

This invention relates to vectors and their use in gene transfer. The vectors are based on retroviruses, adapted so that they cannot package their own RNA, and which can be used as infectious agents to transfer foreign genes, e.g. for somatic gene therapy.

BACKGROUND OF THE INVENTION

Retroviruses are classified in several ways. They are divided into various groups on the basis of their morphology. These groups are A,B,C and D type viruses. They are also classified as belonging to one of three subfamilies, namely oncoviruses, spumaviruses and lentiviruses.

Mason-Pfizer Monkey Virus (MPMV) is a D-type retrovirus first discovered in breast carcinoma tissue from a rhesus monkey. Despite this, and its classification into the oncovirus subfamily, it does not contain an identified oncogene and there is no evidence that it has oncogenic potential.

D-type viruses are distinguished from other retrovirus families such as the C-type viruses. The latter are characterised by capsid assembly at the cell membrane, and include viruses of the lentivirus group, e.g. Human Immunodeficiency Virus (HIV). Morphologically, in their core structure, D-type viruses also differ from B-type viruses such as Mouse Mammary Tumor Virus (MMTV). Thus the D-type viruses are completely distinct from these other types and as an example of this distinction they have specific signals in the form of amino-acid signal sequences in their assembled ICAP which facilitate transport of the ICAP to the cell membrane. For this reason and others they must be considered as a separate group with unique cis and trans-acting regulatory signals. MPMV is also distinguished from C-type viruses by the ability of the virus envelope to activate the human complement system. This leads to lysis of the virus.

Retroviruses are RNA viruses which replicate through a DNA proviral intermediate which is integrated in the genome of the infected host cell. The virion particle contains a dimer of positive-strand genomic RNA molecules. This genomic RNA is the full-length species transcribed from the proviral DNA by the host RNA polymerase II. A proportion of these full length RNAs which encode the gag and pol genes of the virus are translated by the host cell ribosomes, to produce the structural and enzymic proteins required for production of virion particles. The provirus also gives rise to a variety of smaller singly and multiply-spliced mRNAs coding for the envelope proteins and, in the case of more complex retroviruses, a group of regulatory proteins. The genomic (and subgenomic) RNA molecules are structurally similar to cellular mRNAs in having a 5' $m^7G$ cap and a polyadenylated 3' tail.

A series of problems must be addressed for successful packaging of genomic RNA:

The full-length RNA must be packaged preferentially over the spliced viral messages as it is the only one carrying the full complement of genetic information for the next generation of virions. The virus must also specifically select the genomic RNA against the enormous quantity and variety of physically similar host cell mRNAs as, unlike many other viruses, retroviruses do not generally arrest host RNA synthesis. There must be a mechanism whereby genomic RNA to be packaged is recognised such that a proportion is either protected from being translated and transported to an assembly site or is associated with the gag precursor polyprotein for which it has just coded immediately after translation. Lastly, there is the stoichiometric problem of having to package the correct number of genomes in association with 3–4000 gag precursor proteins, adequate numbers of reverse transcriptase molecules, a protease, tRNA primers and, in some cases, multiple copies of regulatory proteins.

Packaging the genome thus entails problems of specificity of selection of RNA and also considerations of RNA compartmentalisation.

The virus overcomes these problems by the presence of cis-acting elements, i.e. "packaging signals", in the viral genomic MRNA. Studies on spontaneously arising and laboratory constructed viral mutants have confirmed that specific sequences are critical for RNA recognition and encapsidation. Linial et al, Cell 15:1371–1381 (1978); Mann et al, Cell 33:153–159 (1983); Watanabe et al, PNAS USA 79:5986–5990 (1979) and WO-A-9119798 disclose that deletions in the 5' untranslated leader sequence lead to defects in packaging in, respectively, Rous Sarcoma Virus (RSV), Moloney Murine Leukemia Virus (MoMLV), Spleen Necrosis Virus (SNV) and HIV.

Deletion mutants have defined sequences necessary for RNA packaging in several retroviruses. In some of these, the extent of the sequence sufficient for packaging has also been mapped. Implicit in the description of packaging signals and RNA secondary structure is the premise that, if this sequence is introduced into heterologous RNA then, theoretically, the heterologous RNA should be encapsidated by retroviral particles. Constraints on packaging include the theoretical one (for which Mann et al, J. Virol. 54:401–407 (1985) provide some circumstantial evidence) that sequences adjacent to the packaging signal (PSI) should not favour the formation of alternative secondary structures disrupting PSI. Additionally, the total length of RNA packaged is physically limited by the capacity of the virus to package RNA of a certain size. In HIV, proviral constructs incorporating heterologous genes have been shown by Terwilliger et al, PNAS USA 86:3857–3861 (1989) to lead to a replication defect when the total length of the viral RNA produced significantly exceeds that of the original virus. The replication defect is consistent with a declining efficiency of RNA packaging.

Nevertheless, there is significant variability between different viruses in the nature and site of their encapsidation sequences. The mechanism of RNA recognition is so poorly understood that theoretically it is not possible to make predictions of the exact site and nature of encapsidation sequences without experimental data. There is none for D-type retroviruses.

The development of retroviral vector systems has been a direct development of the work described above. In these systems, a packaging-defective "helper" virus is used to generate particles which encapsidate a highly modified RNA genome (the vector). Watanabe et al, Mol. Cell Biol. 3:2241–2249 (1983), and Eglitis et al, BioTechniques 6:608–614 (1988), report that vectors containing a minimum of the viral long terminal repeats, the packaging signal and a primer-binding site together with a heterologous marker gene have been encapsidated into virion particles and transferred to the cells for which the parent virus is tropic. By this means, it has been possible to define the minimal sequence required for encapsidation of RNA into a virus particle.

Adam et al, J. Virol. 62:3802–3806 (1988), disclose that, for MoMLV, the sequence sufficient for packaging encompasses the 5' leader region first defined by deletion as leading to a packaging defect. No additional sequences were essential although gag sequences enhanced packaging of the vector.

WO-A-9119798 discloses that an HIV-based vector containing essentially only the 5' leader sequence as a potential packaging signal was reported to be successfully encapsidated by an HIV-based packaging system. This work has not yet been confirmed. Indeed, there has been failure, confirmed herein, to encapsidate HIV RNA containing only the 5' leader sequence.

SUMMARY OF THE INVENTION

According to a first aspect of the present invention, a provirus is capable of producing MPMV proteins but is not replication-competent because the RNA cannot be packaged into virions. Using this packaging-defective provirus vector, packaging-defective cell lines can be created and used to investigate the packaging mechanism of the virus and to develop strategies to interfere with this packaging mechanism. Virions produced by such packaging-negative proviruses may be used for vaccines and as a system for efficiently introducing a desired gene into a mammalian cell. This has also now been successfully achieved for HIV and, therefore, for other lentiviruses, according to a second aspect of the present invention.

DESCRIPTION OF THE INVENTION

The first aspect of the invention relates to MPMV.

MPMV has several potential advantages as a retroviral vector, compared to other retroviruses which have already been used and are being developed as gene vectors for potential use in humans. In particular:

1) It is infectious for all human cells so far assayed
2) It is non-pathogenic in humans
3) It has an envelope susceptible to complement-mediated lysis; this means that if an unlikely event such as a recombination occurred in the production of retroviral vectors for human use there would be no danger from reconstituted MPMV as the virus would be destroyed in vivo as soon as it appeared in the extracellular space
4) The molecular biology and virus assembly functions are well understood
5) It has a genome of greater than 8 kilobases which appears to be largely redundant for packaging function and which could thus be replaced by desired genetic sequences. Most DNA copies of RNAs coding for genes which are candidates for gene therapy would fit into a viral genome of these dimensions
6) There is no apparent detectable homology with endogenous human retroviral sequences, thus minimising the potential for recombination between therapeutic vectors and endogenous sequences leading to replication competent virus arising in vivo
7) There is no evidence that MPMV encapsidates heterologous viral sequences such as the VL30 family encapsidated by murine retroviral vectors and transmitted to all cells infected by murine retroviral vector systems.

The first aspect of the present invention is based on studies of the molecular biology and replication of wild-type and mutant MPMV and defective virus constructs made therefrom (vectors), in which major segments of the coding function have been deleted and replaced with marker genes in order to localise the cis acting signals involved in viral RNA packaging in MPMV. Signals both necessary and sufficient for packaging of RNA into a virion particle have been defined. It appears that the localisation of signals necessary and sufficient for RNA packaging differs from other viruses previously studied, and that the site of these signals could not have been predicted by direct analogy to other retroviruses and study of their packaging mechanism. Vectors have been constructed which themselves are replication-defective but whose RNA can be packaged in trans by wild-type virus and delivered to target cells for which MPMV itself is tropic by infection. These vectors integrate into the target cell chromosome and express the target gene efficiently enough in the case of antibiotic resistance markers to produce target cells which themselves are antibiotic-resistant.

In particular, it has been discovered that it is possible to make MPMV packaging-defective vectors and cell lines. It has been found that the region between the primer-binding site and the 5' major splice donor in MPMV contains sequences necessary for packaging of MPMV RNA into virions. One can prepare a vector comprising a packaging-defective MPMV provirus, wherein the vector contains a nucleotide sequence which corresponds to a sufficient number of nucleotides from an MPMV genome to express desired MPMV products, but does not correspond to a sufficient number of nucleotides corresponding to the region between the primer-binding site and the 5' major splice donor to efficiently package MPMV RNA (the packaging sequence).

These sequences preferably correspond to the genome of MPMV. The term corresponds means that conservative additions, deletions and substitutions are permitted. The primer-binding site (18 bp) and the 5' major splice donor are respectively numbered 348–365 and 475–480 in the genomic nucleotide sequence given by Sonigo et al, Cell 45:375–385 (1986).

Preferably, the vector does not contain the MPMV packaging sequence corresponding to the segment immediately downstream of the primer-binding site and just upstream of the 5' major splice donor. Typically, the vector may contain nucleotides ranging from about 2 bases downstream of the primer-binding site to about 23 to 63 bases downstream of the primer-binding site and still be packaging-deficient. In one embodiment, the packaging sequence absent from the vector contains the 121-base nucleotide sequence shown herein as SEQ ID No. 1. In another embodiment, the packaging sequence comprises the 62-base segment sequence of bases 51 to 112 of SEQ ID No. 1. In another embodiment, it comprises the 23-base segment of bases 28 to 50 of SEQ ID No. 1. SEQ ID No. 1 is GGCGCCCAACG-TGGGGCTGGATACGAGGGAATTTCGTGAGGAAGA-CGACGCGTTCGCCGGCCGGCGATTAAAAGTGAAA-GTAAACTCTCTTGGCCGCCGCGGGAACCTGCCGC-GTTGGACC.

The number of bases that need to be left out of the vector can vary greatly. For example, the given 23-base pair deletion in MPMV is sufficient to result in loss of packaging ability. However, even smaller deletions in this region should also result in loss of packaging efficiency. Indeed, it is expected that a deletion as small as about 5 base pairs in this region should remove efficient packaging ability. The size of a particular deletion can readily be determined based on the present disclosure by the person of ordinary skill in the art.

The vector should contain an MPMV nucleotide segment containing a sufficient number of nucleotides corresponding to nucleotides of the MPMV genome to express functional MPMV gene products, but as described above, should not contain a sufficient number of nucleotides corresponding to the region between the primer-binding site and the 5' major splice donor to permit efficient packaging of the viral RNA into virions. In using these vectors to establish MPMV packaging-defective cell lines it is preferred that such cell lines do not produce any infectious MPMV. Although a cell line transformed by these packaging-defective deficient vectors would have low infectivity because the cells are packaging-defective, some RNA can still be packaged into the virion. Accordingly, it is preferable that the MPMV nucleotide segment does not correspond to the entire MPMV genome so that, if some of the viral RNA is packaged into the virion, what is packaged will not be replication-competent virus.

Preferably, a selected cell line is transformed using at least two different vectors, each containing a different portion of the MPMV genome and also not containing the sequence necessary for viral packaging. Then, by cotransfecting a cell with each vector, the cell would still be able to express all the MPMV structural and enzymatic proteins and produce virions. In one preferred embodiment, the or each vector does not contain sequences corresponding to an MPMV LTR (long terminal repeat sequence) but contains sequences corresponding to a promoter region and/or another genome's polyadenylation sequences. Selection of particular promoters and polyadenylation sequences can readily be determined based upon the particular host cell. Preferably the LTR to which the sequences do not correspond is the 3'LTR.

In one preferred embodiment, one vector includes sequences permitting expression of MPMV proteins upstream of env and the second vector permits expression of the remaining proteins. For example, one vector contains an MPMV nucleotide segment corresponding to a sufficient number of nucleotides upstream of the gag initiation codon to the env gene sequence to express the 5'-most gene products. The other vector contains an MPMV nucleotide segment corresponding to a sufficient number of nucleotides downstream of the gag gene sequence and including a functional env gene sequence. Such vectors can be chemically synthesised from the reported gene sequence of the MPMV genome or derived from the many available MPMV proviruses, by taking advantage of the known restriction endonuclease sites in these viruses by the skilled artisan based on the present disclosure.

Preferably, a different marker gene is added to each vector. Then, using a preselected cell line cotransfected with these different vectors, and by looking for a cell containing both markers, a cell that has been cotransfected with both vectors is found. Such a cell would be able to produce all of the MPMV proteins. Although virions would be produced, the RNA corresponding to the entire viral sequences would not be packaged in these virions. One can use more than two vectors, if desired, e.g. gag/pol vector, a protease vector and an env vector.

Retroviruses can in some cases be pseudotyped with the envelope glycoproteins of other viruses. Consequently, one can prepare a vector containing a sufficient number of nucleotides to correspond to an env gene from a different retrovirus. Preferably, the 5'LTR of this vector would be of the same genome as the env gene. Such a vector could be used instead of an MPMV env packaging-defective vector, to create virions. By such a change, the resultant vector systems could be used in a wider host range or could be restricted to a smaller host range, e.g. using an HIV env gene vector which would restrict the cell range to those bearing the CD4 protein.

Virtually any cell line can be used. Preferably, a mammalian cell line is used, for example CV-1,Hela, Raji, SW480 or CHO.

In order to increase production of the viral cellular products, one could use a promoter other than the 5' LTR, e.g. by replacing the 5' LTR with a promoter that will preferentially express genes in CV-1 or HeLa cells. The particular promoter used can easily be determined by the person of ordinary skill in the art depending on the cell line used, based on the present disclosure.

In order to enhance the level of viral cellular products, one can also add enhancer sequences to the vector to get enhancement of the MPMV LTR and/or promoter. Particular enhancer sequences can readily be determined by a person of ordinary skill in the art depending on the host cell line.

By using a series of vectors that together contain the complete MPMV genome, one can create cell lines that produce a virion that is identical to the MPMV virion except that the virion does not contain MPMV RNA. These virions can readily be obtained from the cells. For example, the cells are cultured and the supernatant harvested. Depending on the desired use, the supernatant containing the virions can be used or these virions can be separated from the supernatant by standard techniques such as gradient centrifugation, filtering etc.

These attenuated virions are extremely useful in preparing a vaccine. The virions can be used to generate an antibody response to MPMV virions and, because these virions are identical to the actual MPMV virions except that the interior of these virions do not contain the viral RNA, the vaccine created should be particularly useful. Pseudotyped virions produced from cell lines cotransfected with MPMV gag/pol and protease genes and containing the env gene from another virus may be useful in creating a vaccine against this other virus. For example, an HIV env vector in the cell may give rise to a viral particle with an HIV env capable of eliciting an antibody response to HIV but without pathogenicity because of the absence of any other HIV proteins or HIV RNA.

These virions can also be used to raise antibodies to the virion that can then be used for a variety of purposes, e.g. screening for the virion, developing target systems for the virions etc. Additionally these MPMV packaging-deficient cell lines can be extremely useful as a means of introducing a desired gene, for example a heterologous gene into mammalian cells, as described below.

These virions may be used as an extremely efficient way to package desired genetic sequences and deliver them to target cells infectable by MPMV. This may be done by preparing a vector containing a nucleotide segment containing a sufficient number of nucleotides corresponding to the packaging nucleotides of MPMV (MPMV packaging region), a predetermined gene and, flanking the packaging sequence and predetermined gene, sequences corresponding to a sufficient number of sequences from within and near the LTR for packaging, reverse transcription, integration of the vector into target cells and gene expression from the vector.

The packaging region preferably corresponds to at least the region between the primer-binding site and the major 5' splice donor. With regard to the experimental data presented below concerning the packaging of such a vector, the vector might also have the first 500 bp of the gag gene sequence of MPMV in order to enhance packaging efficiency. Further, it might specifically not include nucleotides corresponding to the sequence numbered 481–493 between the 5' major splice donor and the gag gene initiation codon, as absence of this sequence which appears to inhibit packaging might render the vector more packageable. For example, a sufficient number of MPMV sequences to be packaged, reverse-transcribed, integrated into and expressed in the target cells would include the U3,R and U5 sequences of the LTRs, the packaging sequences and some sequences flanking the LTRs (required for reverse transcription). Although the packaging sequences described between the primer-binding site and the 5' major splice donor would be sufficient for packaging such a vector, it may be advantageous to include the first 500 nucleotides of the gag gene coding sequence as this appears to enhance packaging further, and it would be advantageous to omit the region corresponding to the sequence between the 5' major splice donor and the gag initiation codon. Mutation of the gag initiation codon would be acceptable to avoid translation starting from this point whilst still retaining the cis acting gag nucleotide sequence required for packaging. For example, the gag ATG could be mutated to ATC by site-directed mutagenesis.

When this vector is used to transfect one of the MPMV packaging-deficient cells, it is the nucleotide sequence from this vector that will be packaged in the virions. These MPMV packaged genes may then be targeted to cells infectable by MPMV. This method of transformation is expected to be much more efficient than current methods. Further, by appropriate choice of genes, the method of MPMV infection may be monitored.

For example, the vector could contain a sufficient number of nucleotides corresponding to both 5' and 3' LTRs of MPMV to be expressed, reverse-transcribed and integrated, a sufficient number of nucleotides corresponding to the MPMV packaging sequence to be packaged, for example a segment between the primer-binding site and the 5' major splice donor. The vector would also contain a sufficient number of nucleotides of the gene which is desired to be transferred to produce a functional gene (e.g. gene segment). This gene can be any gene desired, as described below.

The infectious proviral clone of MPMV pSHRM15 has been described by Weiss et al (ads.) in RNA Tumor Viruses, pub. Cold Spring Harbor. It comprises a complete provirus together with a hygromycin-resistance gene in the flanking sequence (FIG. 3). Using oligonucleotide site-directed mutagenesis, a series of segments in the non-coding region has been deleted, between the primer-binding site (PBS) and the gag initiation codon. Deletion MPS1 encompasses the complete region from PBS to major splice donor, namely deletion from nucleotides 356–469 (SD). MPS2 comprises a deletion of the 5' region of the MPS1 deletion, namely from nucleotides 376–432, and MPS3 the 3' region of the MPS1 deletion, namely 403–464. MPS4 is a deletion between the SD and the gag initiation codon, namely from nucleotides 481–493. All of these nucleotide numberings refer to the numbering as used by Gerwin et al, J. Virol. 24:478–488 (1977).

These deletions in a subcloned fragment of pSHRM15 were subcloned back into the intact infectious provirus (see FIG. 2 for summary). The same deletions were also cloned into a defective derivative of pSHRM15 comprising the two long terminal repeat sequences and 3' sequences from the Dra11 site in the envelope gene. At the 5' end, the 5' leader sequence extending to include 1.5 kB of the gag gene was included; between these was cloned a Hygromycin phosphotransferase gene cassette under control of an SV40 early promoter sequence in sense relative to the vector (FIG. 3). Into the 5' leader sequence was cloned one of the MPS1, 2, 3 and 4 deletions. Subsequent deletions were made in the gag gene such that either the 5' 0.5 kB of gag remained.

Combinations of wild-type vector and deletion mutant provirus or deletion mutant vector and wild-type virus or deletion mutant vector and deletion mutant provirus were cotransfected into Cos 1 cells. The supernatants were filtered and plated on to Hela cells and the number of hygromycin-resistant colonies arising demonstrated efficiency of packaging of the hygromycin-containing vector. In effect, competition for packaging of RNA was established between vector and virus and the effect of deletion mutants in either vector or provirus on the balance of full length RNAs packaged was determined.

In summary, and as reported also in Example 1, deletion MPS1 led to virtual abolition of RNA packaging. MPS2 and MPS3 showed a packaging defect of equal severity and MPS4 did not affect packaging at all. In fact, vectors containing the MPS4 deletion appeared to package at a greater efficiency than did those with an intact region from SD to gag AUG. Deletion of gag sequence to leave only the 5' 0.5 kB led to an increase in packaging efficiency, suggesting that sequences in the distal region which were deleted have an inhibitory effect on RNA encapsidation.

It may be concluded that MPMV has a packaging signal requirement which is unique amongst retroviral packaging signals so far described, in that sequences between SD and gag ATG which (except for RSV) are almost universally required for packaging in other viruses are dispensable in MPMV and, on removal, lead to enhancement of packaging. Thus a vector to be efficiently packaged preferably does not contain the nucleotides corresponding to those nucleotides between the SD and the gag initiation codon. Packaging can be obtained with sequences contained in the 5' half of the PBS-SD region and the first 0.5 kB of the gag gene, which distinguishes it from RSV. The region of gag 3' to the first 500 nucleotides apparently also has a relative inhibitory effect on encapsidation and is preferably excluded from a vector to be efficiently packaged.

These findings are unique, in terms of definition of retroviral packaging signals, in the description both of signals which are necessary and sufficient for packaging and in the description of competition of RNA for packaging, and also the identification of signals which lead to a decrease in viral packaging (which may be termed inhibitory signals). The present disclosure allows someone skilled in the art to construct an efficient retroviral vector system based on MPMV.

The second aspect of the invention relates to HIV and other lentiviruses. It is based on studies analogous to those described above for MPMV. Although results are reported, and the invention illustrated, with respect to HIV, it is believed that the same applies to other lentiviruses.

The results for HIV include the surprising finding that the 5' leader sequence is clearly not sufficient to encapsidate a vector. It has now been established that, for encapsidation to occur at all, a second sequence in the virus 3' of the tat splice acceptor must be included. This region has been further mapped down to a segment from bases 7621–8141 (according to the Los Alamos AIDS database); these encompass very closely the boundaries demonstrated for the REV responsive element. In the presence of these two sequences, a vector can be encapsidated at an efficiency of 88% that of the wild-type virus, when the relative levels of expression of the vector in the cell line and encapsidated in virions is compared. Vectors which in addition contain the gag gene and the 3' of envelope, segment already described, in the presence of the REV protein expressed in cis or trans are expressed at a higher level in cells and this increased abundance leads to an increased availability of RNA for packaging. Thus the presence of the gag gene with the correct extra genetic factors will lead to an enhanced packaging and delivery of an HIV-based vector. The analysis of this packaging efficiency has shown that the gag gene is, however, dispensable for packaging but may have an enhancing function.

The surprising discovery has been made that, when the gag gene is deleted, packaging is reduced, but that when a heterologous sequence replaces the gag gene, the packaging efficiency is dramatically reduced. Thus, inserting heterologous genes within the proviral genome in place of the gag gene can in some cases make encapsidation unusably inefficient. It is also now clear that the presence of the rev responsive region (RRE) within a vector is advantageous. This might have been predicted in terms of the ability of the rev/RRE system to enhance export of unspliced viral RNA from the nucleus. However, it has now been demonstrated that the presence of the RRE in a vector enhances its capacity for transduction by a helper virus system. This appears to be a direct effect of enhancement of packageability of the RNA and is an unexpected function of the rev/RRE system.

The present invention includes within its scope lentivirus vectors which themselves are replication-defective, but whose RNA can be packaged in trans by wild-type virus and delivered to target cells for which HIV itself is tropic by infection. These vectors integrate into the target cell chromosome and express the target gene efficiently enough, in the case of antibiotic-resistance markers, to produce target cells which themselves are antibiotic-resistant.

Specifically, a novel vector comprises a sufficient number of nucleotides corresponding to an HIV genome to express functional HIV gene products, but which does not contain a sufficient number of nucleotides corresponding to nucleotides of the HIV genome to produce infectious virus. Vectors have been identified that contain a sufficient number of nucleotides corresponding to an HIV genome to be encapsidated into HIV virion particles, but which do not contain a sufficient number of nucleotides corresponding to nucleotides of the HIV genome to produce HIV gene products required for production of infectious HIV virions.

More specifically, the sequences which must be included in such a vector appear to be those nucleotides corresponding to the untranslated region of HIV between the major splice donor site and the initiation codon for the gag gene suggested in WO-A-9119798 to be sufficient for vector encapsidation. These signals alone are not sufficient for vector encapsidation; however, in the presence of the nucleotide sequence of HIV (HXB2R) numbering from 7167 to 8267 (numbered as from the Los Alamos AIDS database), a sequence which encompasses the rev responsive element (RRE), vector encapsidation does occur. This encapsidation is still very inefficient if the gag gene is replaced by heterologous sequences such as those encoding the chloramphenicol acetyl transferase gene. However the inclusion of cis-acting gag sequences 5' of the BglII site at nucleotide 1642 (numbered according to the Los Alamos database) will enhance packageability of vectors containing the 5' untranslated region and the RRE between 3 and 6-fold, as set out in Example 3, below.

Vectors containing all three of these important cis-acting sequences are capable of having cloned into them genes which may be of therapeutic use. Vectors containing the 5' untranslated region and the RRE can be encapsidated, the presence of the RRE conferring enhancement of encapsidation greater than could have been predicted from its effects on the transport and stability of unspliced RNA alone. Suitable genes may be cloned into such vectors and delivered to desired target cells.

However, there may be serious decreases in packageability and transducibility if heterologous sequences are inserted in place of the gag gene sequence. This finding alters considerably the potential design of vectors which might transfer therapeutically useful heterologous genes.

The second aspect of the present invention utilises a packaging-defective HIV provirus as part of a vector containing a nucleotide sequence which corresponds to a sufficient number of nucleotides from an HIV genome to express desired HIV products, but does not correspond to a sufficient number of nucleotides corresponding to the region between the primer-binding site and the 5' major splice donor to efficiently package HIV RNA (the 5' packaging sequence). The conserved stable secondary structure of the HIV-1 packaging signal and major splice donor region is described by Harrison et al, J. Virol. 66:4144–4153 (1992), the content of which is incorporated herein by reference.

Such a packaging-defective provirus is capable of production of HIV virion particles but incapable of encapsidating its own RNA within these particles. This defective provirus can also be separated into two coding plasmid constructs containing complementary gene sequences of HIV which between them are sufficient to produce all the essential structural, enzymatic and regulatory proteins of HIV. A possible arrangement has one construct coding for the gag and pol gene products and the other coding for the env, tat and rev gene products. Neither of these constructs would include the 5' leader sequence which is necessary for encapsidation and hence would be incapable of packaging its own RNA but could package in trans RNA from a suitable vector which did contain the three important packaging signal sequences which have now been defined. Similarly, vectors can be prepared corresponding to a sufficient number of nucleotides from an HIV genome to contain the packaging signals described herein, but to contain no other HIV-coding gene sequences. This vector can then be packaged in trans by the proteins derived from the defective provirus which has deleted packaging signals and the vector then delivered to target cells normally infectable by wild-type HIV.

These sequences preferably correspond to the genome of HIV. The term corresponds means that conservative additions, deletions and substitutions are permitted.

As indicated above, retroviruses can in some cases be pseudotyped with the envelope glycoproteins of other viruses. Consequently, one can prepare a vector containing sufficient number of nucleotides to correspond to an env gene from a different retrovirus. Preferably, the 5' LTR of this vector is of the same genome as the env gene. Such a vector could be used instead of an HIV env packaging-defective vector to create virions. By such a change, the resultant vector systems could be used in a wider host range of target cells.

As indicated above for MPMV, virtually any cell line can be used. Preferably, a mammalian cell line is used, for example CV-1,Hela, Raji, SW480 or CHO.

In order to increase production of the viral cellular products, a different promoter may be used, as described above for MPMV.

In order to enhance the level of viral cellular products, enhancer sequences can be added, as described above for MPMV.

By using a series of vectors that together would contain the complete HIV genome, one can create cell lines that produce a virion that is identical to the HIV virion except that the virion does not contain HIV RNA, as described above for MPMV.

These attenuated virions are extremely useful in preparing a vaccine, raising antibodies etc., as described above for MPMV. In particular, these virions may be used as an extremely efficient way to package desired genetic sequences and deliver them to target cells infectable by HIV. This may be done by preparing a vector containing a nucleotide segment containing a sufficient number of nucleotides corresponding to the packaging nucleotides of HIV (HIV packaging regions), a predetermined gene and, flanking the packaging sequence and predetermined gene, sequences corresponding to a sufficient number of sequences from within and near the LTR for packaging, reverse transcription, integration of the vector into target cells and gene expression from the vector.

In either aspect of the invention, the foreign gene to be delivered can be any gene desired, for example the gene for neomycin phosphotransferase ($Neo^R$) or the gene for Hygromycin phosphotransferase ($Hygro^R$). More preferably, the gene expresses a product which is of therapeutic value in patients deficient for the gene, such as the gene for adenosine deaminase (ADA), for Aryl sulphatase A, or for the B domain-deleted factor VIII, which are defective in patients with, respectively, ADA deficiency, metachromatic leucodystrophy and haemophilia. They may be cloned into the vectors and delivered to desired target cells. The gene may express a product that adversely affects the replication of a pathogenic organism such as a trans-dominant inhibitor, an inhibitor of viral integration, an anti-sense RNA, a catalytic RNA or a soluble viral receptor derivative such as soluble CD4.

The gene may have a therapeutic use, such as the presentation of an antigenically important epitope of a pathogen or of a tumor cell on the target cell surface, in order to stimulate a protective or otherwise beneficial immune response against such a pathogen or tumor. The gene may encode the antigen recognition segment of the T lymphocyte receptor molecule such that, when lymphocytes are transformed with this vector, they express T cell receptors of the desired antigenic specificity. Such T cell receptor specificity is preferably directed against the important epitopes of either a pathogenic microorganism or against a tumor-specific antigen. Clonal expansion of such T cells (monoclonal T cells) would be useful as a therapeutic modality against infectious pathogens and as an agent against malignant disease.

Given the previously unknown data regarding packaging signals in MPMV and HIV which have been identified, those skilled in the art may construct another packaging-defective MPMV or HIV which is unable to encapsidate its own RNA but which is able to code for all the essential viral structural and enzymatic proteins to create a virus particle deficient in viral RNA. Those skilled in the art may now also construct vectors which have the required cis-acting sequences such that they would be encapsidated into such genomic RNA defective particles and delivered to target cells for which the virus is normally tropic. The RNA of the vector would then be reverse-transcribed by the virion reverse transcriptase enzyme and integrated into the cellular DNA by the viral integrase enzyme. Those skilled in the art with and only this information could thus create a retroviral vector system based on MPMV or HIV. This system is potentially improved by the use of heterologous genetic promoter sequences within the vector and by the use of tissue-specific sequences such as tissue-specific promoters or intron sequences defining expression of the gene in a particular tissue.

Preferably, a promoter for the desired gene is included, although the LTR sequence itself can serve as a promoter. Virtually any promoter can be used, but preferably it facilitates expression of the gene in the host cell to which the gene is transferred. Preferred promoters include viral promoters, such as SL-3, murine retroviral LTR etc. Enhancer sequences are also preferably used in the vector. Polyadenylation sequences for the gene are preferably included. In the case of a gene in the sense orientation with respect to the vector, this function could be achieved by the 3' LTR. In the case of a gene in anti-sense with respect to the vector, an additional polyadenylation signal at the 3' end of the gene (i.e. in anti-sense to the vector) is preferably incorporated. The vector can contain more than one gene or pseudogene sequence, permitting the expression of multiple genes of interest.

This vector can preferably be used with the packaging-defective vectors described above. In such a situation, MPMV/HIV LTRs are preferably in the vector corresponding to the genome of the packaging-deficient vector, to facilitate packaging efficiency. However, in addition to use with packaging-defective virus, this vector can also be used with helper virus for gene transfer.

The present invention is further illustrated by the following Examples. These Examples are provided to aid in the understanding of the invention and are not to be construed as limitation thereof. Example 1 relates to MPMV-based vectors, and Example 2 to HIV-based vectors.

The Examples refer to the following references, the contents of which are incorporated herein by reference:

(1) Rhee et al (1990) J. Virol. 64:3844–3852.
(2) Sonigo et al (1986) Cell 45:375–385.
(3) Terwilliger et al (1989) PNAS USA 86:3857–3861.
(4) Rosen et al (1986) J. Virol. 57:379–384.
(5) Maddon et al (1986) Cell 47:333–348.
(6) Fisher et al (1985) Nature (London) 316:262–265.
(7) Losardo et al (1990) J. Virol. 64:1756–1763.
(8) Morgenstern et al (1990) Nucleic Acids Res. 18:3587–3596.
(9) Sorge et al (1983) J. Virol. 48:667–675.
(10) Chomczynski et al (1987) Anal. Biochem. 162:156–159.
(11) Feinberg et al (1983) Anal. Biochem. 132:6–13.
(12) Kingston (1987) in Current Protocols in Molecular Biology, Volume 1, Greene Publishing Associates and Wiley Interscience, New York.
(13) Potts (1990) Techniques in HIV Research. Stockton press, New York, pp. 103–106.
(14) Kowalski et al (1987) Science 237:1351–1355.
(15) Shimada et al (1991) J. Clin. Invest. 88:1043–1047.
(16) Lever et al (1989) J. Virol. 63:4085–4087.
(17) Selden (1987) Transfection using DEAE-dextran, unit 9.2. Current Protocols in Molecular Biology, Volume 1. Greene Publishing Associates and Wiley Interscience, New York.

The Examples refer also to the accompanying drawings.

EXAMPLE 1

Figure 1:
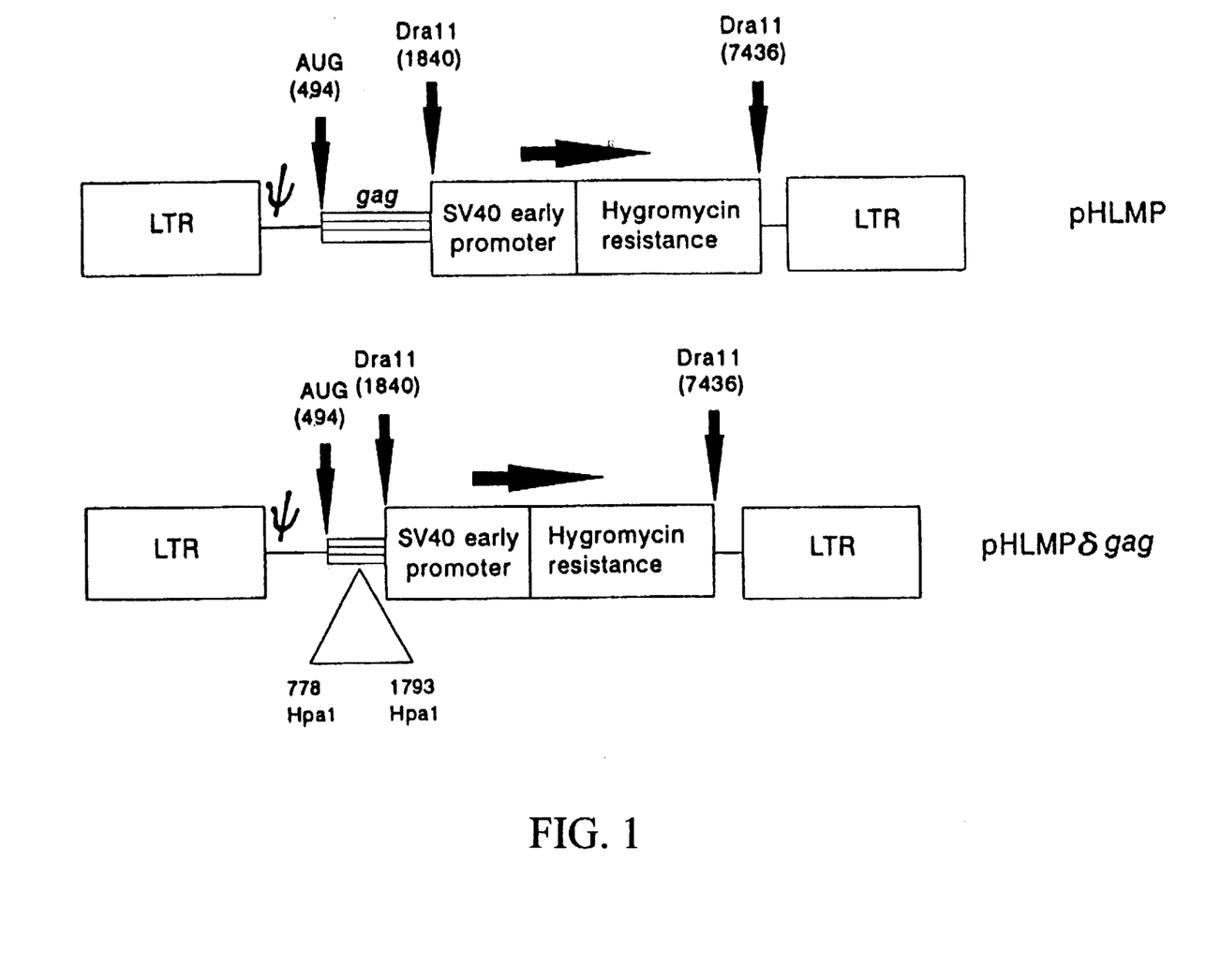
FIG. 1 shows the pHLMP and pHLMPδgag vectors, the latter being the former with a deletion in gag.
Figure 2:
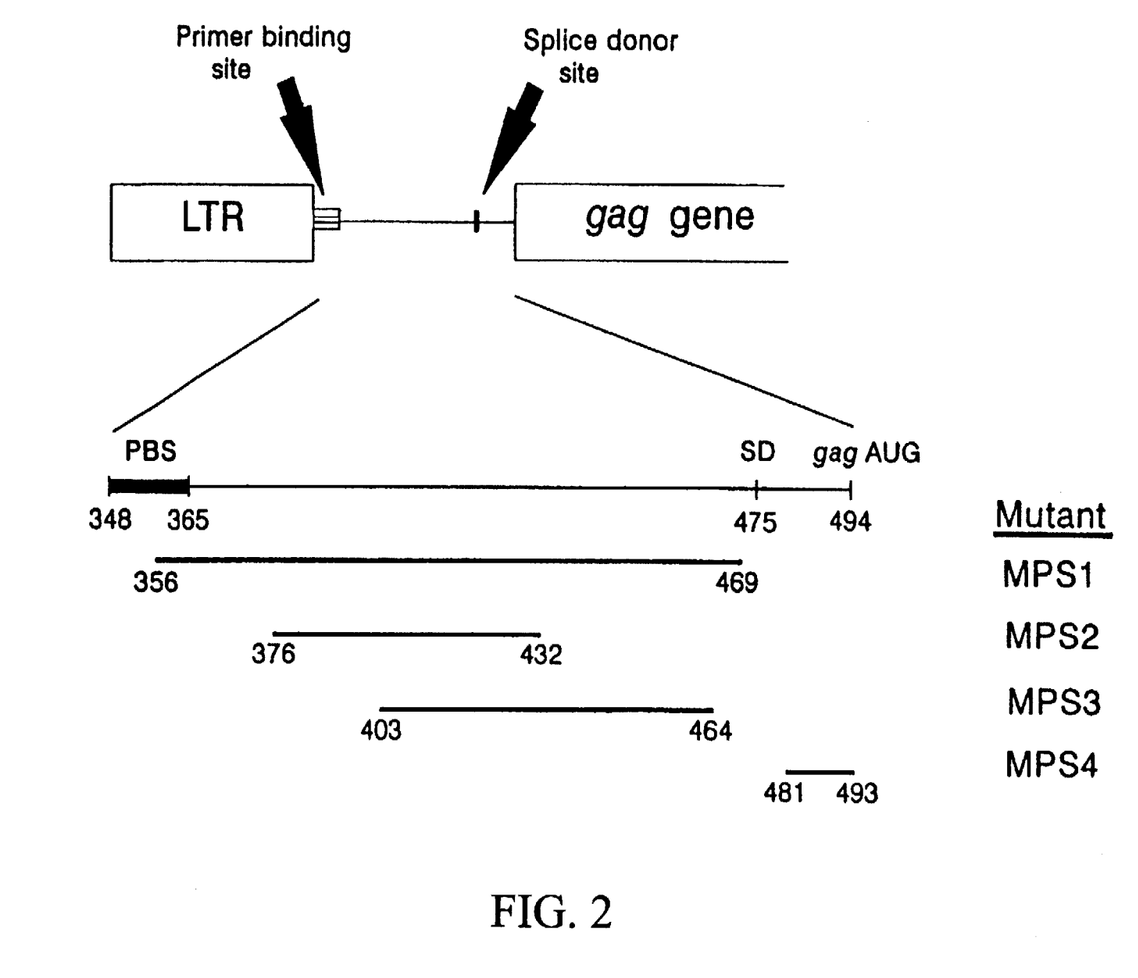
FIG. 2 is a diagram of deletion mutants MPS1 etc.
Figure 3:
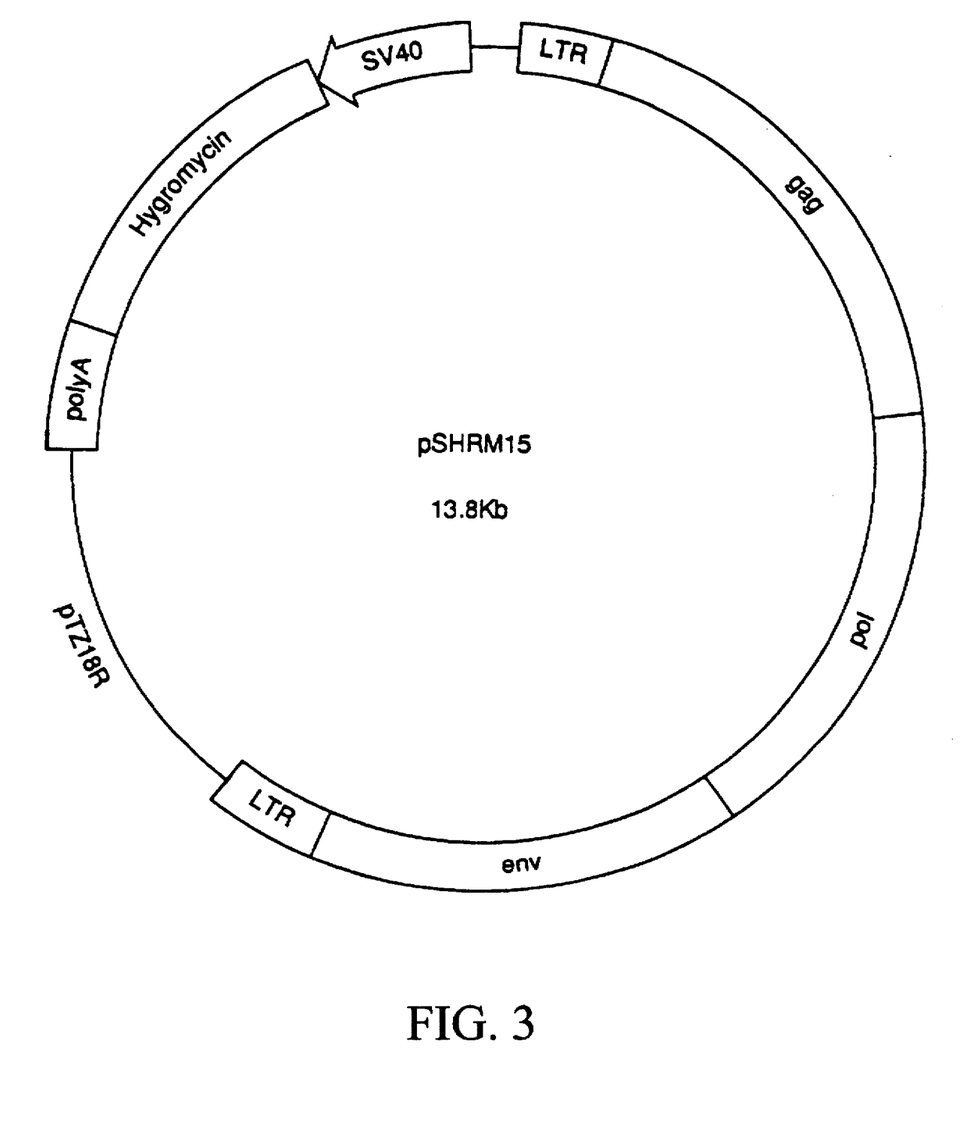
FIG. 3 is a diagram of pSHR15, a plasmid containing the MPMV provirus and based on a pTZ18R backbone with a Hygromycin B resistance gene (Hygromycin) driven by an SV40 early promoter sequence and with an SV40 polyadenylation signal (LTR, gag, pol, env segments refer to virus nucleotide sequences).

In this Example, the proviral clone pSHRM15 previously described (FIG. 3) was used as a helper virus to provide in trans all the structural and enzymatic proteins of the MPMV virion. A small vector was constructed, containing the MPMV 5' LTR sequence, the 5' leader sequence down to the BalI restriction site at position 1320 in the gag open reading frame, followed by the Hygromycin B resistance gene in anti-sense orientation to the vector, without a polyadenylation sequence, and finally the 3' terminal of the MPMV provirus from the Dra11 site at 7440 extending to the end of the 3' LTR (FIG. 3). The helper virus and/or the vector have had introduced into them the various deletions previously described, i.e. MPS1, MPS2, MPS3 or MPS4. Vector and helper have been cotransfected into Cos-1 cells and the resulting virions harvested and used to infect Hela cells. The Hela cells have then been maintained in a medium containing the antibiotic Hygromycin and the number of colonies resistant to the drug in which the vector must have been integrated then counted. This gives a measure of the packageability of the vectors and the role of the sequences deleted in encapsidation of RNA into the virion particle.

In a first experiment, vector pHLMP was cotransfected into Cos-1 cells with the pSHRM15 proviral DNA either in its wild-type form or with the MPS1, 2, 3, or 4 deletions in the 5' untranslated region. 48 hours later, the supernatants from the transfections were harvested and used to infect Hela cells and, after 24 hours, the cells were begun on selection with Hygromycin B (Hyg.). The results are given in Table 1:

TABLE 1

| Mutant | Colonies/ml |
|---|---|
| Wild-Type | 12 |
| MPS1 | 106 |
| MPS2 | 129 |
| MPS3 | 157 |
| MPS4 | 15 |
| HLMP | 0 |

It is clear that HLMP cannot transfer alone and that wild-type virus is a poor helper compared to mutants MPS1, 2 and 3. Since all of these latter produce normal virion proteins, it must be concluded that the wild-type viral RNA is competing with the vector RNA for encapsidation.

It is also noticeable that the MPS4 deletion acts like the wild-type, suggesting that this can package itself as well as wild-type and that no important cis-acting sequences involved in packaging are present between the SD and the gag initiation codon. MPS1, 2 and 3 mutations have disrupted a significant part of the packaging signal, hence they do not compete with HLMP for packaging.

In a second experiment, the first was repeated except that the pHLMP vectors also had mutations introduced into the 5' packaging region. Thus, Hygromycin-containing vectors were cotransfected with helper viruses, either or both of which had deletions in the packaging region. Results, given in Table 2, refer to Hygromycin-resistant colonies obtained after infection of supernatants from these transfections on to fresh Hela cells and Hygromycin B selection.

TABLE 2

| | Hygromycin-containing vector | | | | | |
|---|---|---|---|---|---|---|
| Helper | None | HLMP | HLMPS1 | HLMPS2 | HLMPS3 | HLMPS4 |
| WT | 0 | 0 | 0 | 2 | 5 | 20 |
| MPS1 | 0 | 51 | 0 | 0 | 0 | 61 |
| MPS2 | 0 | 94 | 0 | 3 | 79 | 230 |
| MPS3 | 0 | >230 | 25 | 26 | 250 | >400 |

With WT helper virus, very little if any alternative RNA is packaged. The MPS4 deletion however seems to be advantageous for packaging the vector, suggesting that there are sequences in this region which may actually have a negative effect on packaging. HLMPS1 and HLMPS2 package and transfer extremely poorly, suggesting that this is the region of greatest importance for RNA encapsidation. HLMPS3 appears to package as well as HLMP. Although quantitatively different, the results using MPS3 are qualitatively the same and the numbers probably reflect variations between titres of virions obtained after transfection. HLMPS1 has a deletion in its primer-binding site and must have recombined with MPS3 to achieve transfer in this experiment.

In a third experiment, the sequence between the Hpa 1 sites at positions 778 and 1793 in the gag coding region of the HLMP vector was deleted, to see whether this led to enhanced or reduced vector packaging. The deletion leaves intact the first 0.5 kB of gag coding sequence only. The resulting plasmid is called pHLMPδgag. The results are shown in Table 3.

TABLE 3

| | Vector | | |
|---|---|---|---|
| Helper Virus | HLMP | HLMP δ gag | HLMP δ gag |
| Wild-type | 33 | 88 | 67 |
| MPS1 deletion | 92 | 240 | 250 |
| MPS2 deletion | 94 | >400 | >400 |
| MPS3 deletion | 143 | >400 | >400 |
| MPS4 deletion | 78 | >400 | 194 |

The deletion in the gag coding sequence clearly leads to enhanced packaging of the HLMP vector, suggesting that the region 3' of the Hpa 1 site at 1793 in gag has an inhibitory effect on RNA encapsidation.

In a fourth experiment, the third was repeated but using standardisation of infectiousness of supernatants by measuring reverse transcriptase (RT) as a quantitation of the number of virus particles being transferred; see Table 4. RT is measured by scintillation counting of the incorporation of radio-labelled TTP into a polyA template and expressed as radioactive counts per minute (cpm).

TABLE 4

| Helper | Vector | RT-cpm/ml | Colonies/ml | Colonies/100 cpm |
|---|---|---|---|---|
| WT | HLMP | 41840 | 22 | 5 |
| WT | HLMP δ gag | 28152 | 60 | 21 |
| MPS1 | HLMP | 2370 | 92 | 390 |
| MPS1 | HLMP δ gag | 3122 | 500 | 1600 |

The effect of deleting the gag sequence has been quantified; it leads to an approximate 4-fold increase in the packaging of pHLMP. The helper virus competition for packaging is also clearly seen as WT virus allows for the packaging of approximately 60-fold less HLMP vector than does the MPS1 deletion mutant.

EXAMPLE 2

Cells and viruses:

The cell lines Jurkat, Jurkat-tat (4) and Hela T4 (5) were grown in RPMI 1640 supplemented with 10% fetal calf serum, penicillin and streptomycin. These cell lines and the HIV-1 isolate HTLV-III$_B$ were supplied by the Medical Research Council (UK) AIDS Reagent Programme.

Figure 4:
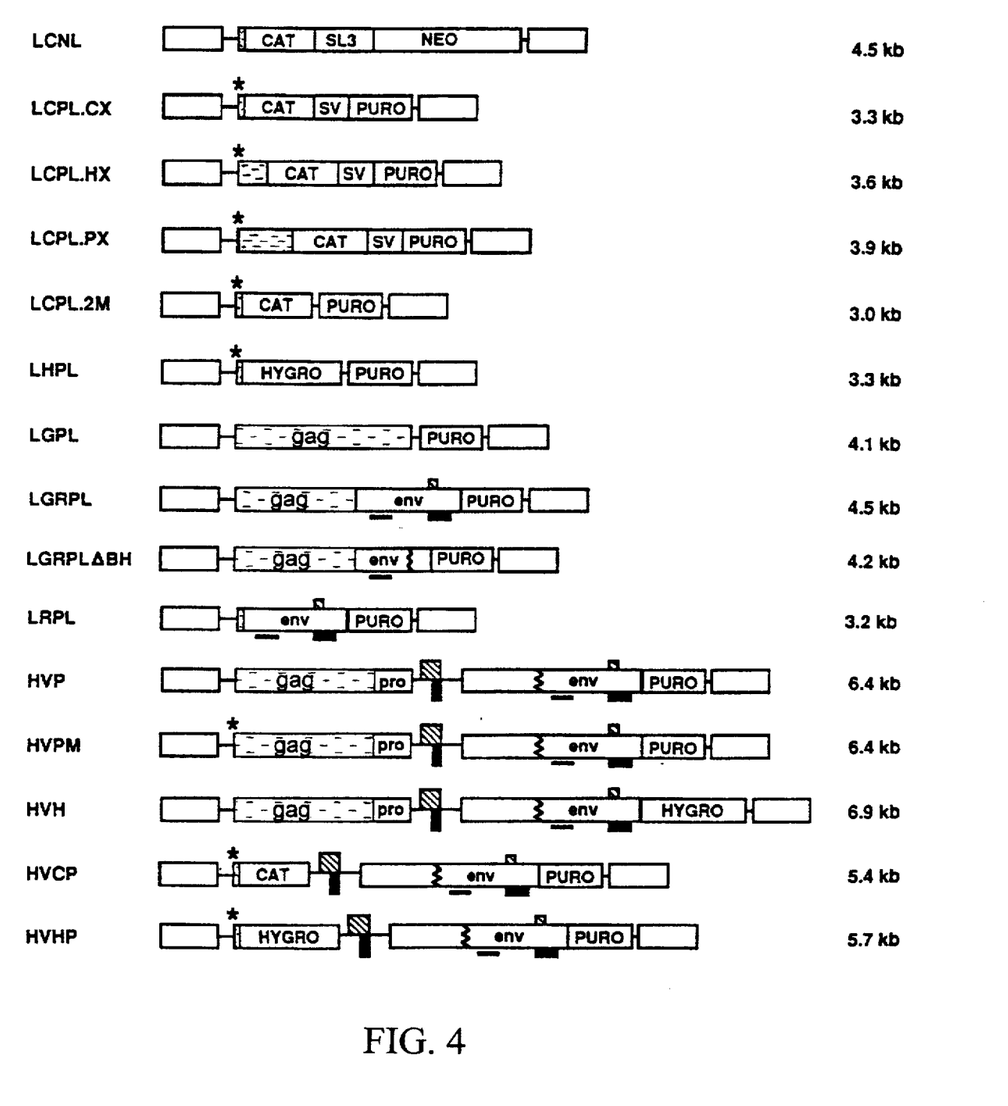
FIG. 4 shows HIV-1 vectors (unlabelled boxes at each end are LTRs. Asterisks denote a mutated gag initiation codon. Hatched and filled boxed represent exons of tat and rev respectively. The Rev-responsive element in env is underlined. Boxes interrupted by a wavy line contain partial deletions. Boxes marked SL3 and SV are SL3-3 LTR and SV40 early promoters).
Figure 5A:
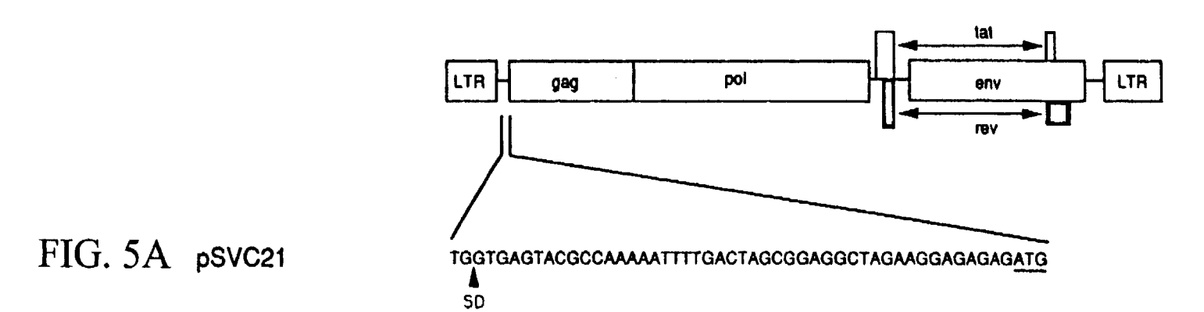
FIG. 5 shows packaging plasmids (i) to (v) described below.
Figures 5B, 5C:
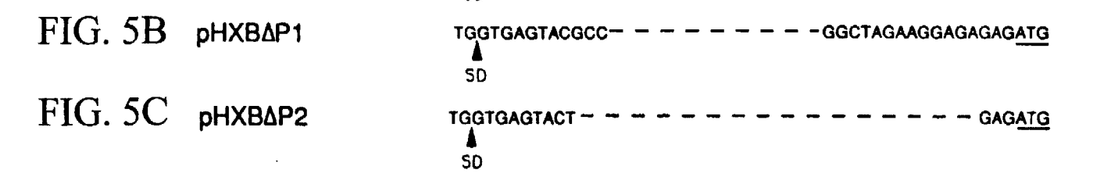
Figure 5D:
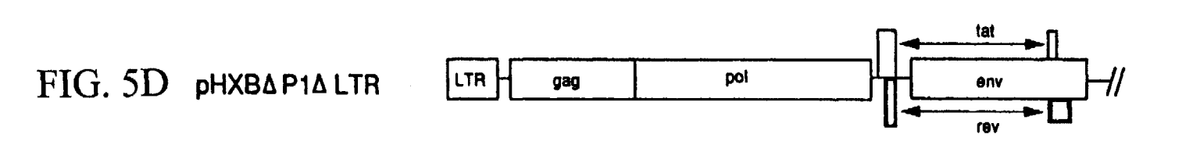
Figure 5E:
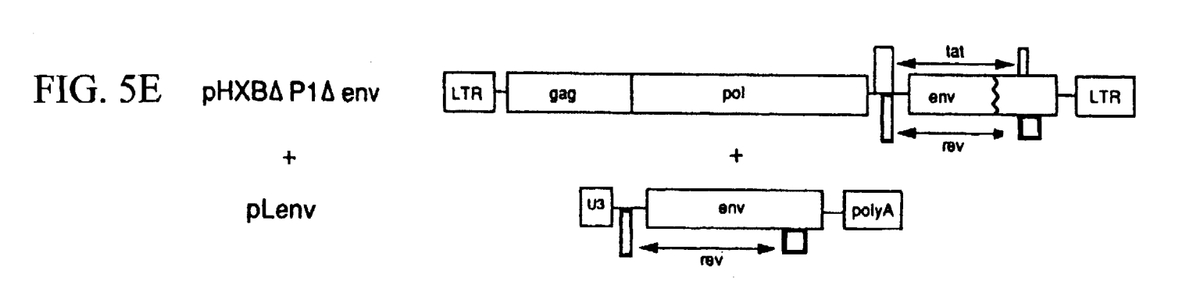

Vectors (see FIG. 4):

All vectors were derived from pSVC21, an infectious proviral clone of the HTLV-lllB isolate originally from a plasmid (pHXBc2) supplied by Drs R Gallo and F Wong-Staal (6). pSVC21 incorporates an SV40 origin of replication. The vectors are illustrated in FIG. 4. In some vectors, the gag initiation codon has been altered by oligonucleotide-directed mutagenesis from GAGATGGGT to GAG-TATACT. Restriction sites, where given, refer to positions in the HXBc2 genome (Los Alamos database numbering, where position 1 is the first base of the 5' LTR).

LCNL. HIV sequences between ClaI (830) and KpnI (9015) were replaced by chloramphenicol acetyl transferase (CAT) and G418 resistance (neo) genes. CAT is expressed using the 5' LTR promoter and neo using a promoter from the murine leukaemia virus SL3-3 (7) in sense (LCNL+) or antisense (LCNL−).

LCPL.CX, LCPL.HX, LCPL.PX. These vectors contain a CAT gene expressed from the 5' LTR and a puromycin gene (puro) driven by the SV40 early promoter (derived from pBabe Puro (8)). The CAT-SV40-puro cassette replaces a ClaI-KpnI fragment (830-9015) in LCPL.CX, a HindIII-KpnI fragment (1085-9015) in LCPL.HX and a PstI-KpnI fragment (1415-9015) in LCPL.PX.

LPL.CX, LPL.HX, LPL.PX. These were derived from the above three vectors by excision of the CAT gene.

LNL. This is similar to LPL.CX with an SL3-Neo-SV40 polyA cassette in place of puro. It is described in WO-A-9119798 as HVB.

LCPL2M, LHPL. LCPL2M is identical to LCPL.CX except that the internal SV40 promoter is replaced by a 43 bp EcoR1-Sal1 fragment (5743-5786) of pSVC21 containing the tat splice acceptor site. In LHPL, a hygromycin-resistance gene (hygro) from pLG90 is substituted for the CAT gene of LCPL2M.

HVP, HVPM, HVH. In these vectors, a Ball-EcoR1 fragment (2689-5743) of SVC21 is deleted, removing the reverse transcriptase and integrase domains of pol, and a BglII fragment within env (7041-7621) is also removed. A Not1 site was introduced by linker insertion at a previously-created XbaI site near the 3' end of env (9). Promoterless puro (HVP) and hygro (HVH) genes were inserted in a position analogous to the nef gene, between this Not1 site and an Xho1 site at 8897. Cells containing HVP and HVH vectors express and process gag p55. HVPM has a mutated gag initiation codon but is otherwise identical to HVP.

HVCP, HVXP. The BssHII (708)-Sal1 (originally 5786) fragment of HVP was replaced by the equivalent fragment from LCPL2M or LHPL. The inserted fragments restore the 5' leader region and tat splice acceptor site but result in the replacement of gag sequences with CAT (HVCP) or hygro (HVHP).

HVPΔEC. In this vector a Cla1 (830)-EcoR1 (formerly Ball, 2689) fragment containing most of the gag-pro region is deleted from HVP.

LGPL, LGRPL, LGRPLΔBH, LRPL. LGPL was derived from HVP by deleting sequences between Sal1 (5786) and the Not1 site referred to above. The puro gene is expressed using the tat splice acceptor and all env, tat and rev sequences are removed. LGRPL was made by deleting HVP sequences between BglII sites in gag and env (2096-7621). This results in an out-of-frame gag-env fusion and the loss of tat and rev functions, but the Rev responsive element is retained. LGRPLΔBH was derived from LGRPL by deleting a HindIII-BamH1 fragment (8141-8475) containing the second exons of tat and rev. LRPL was constructed by deleting HVP sequences between Cla1 (830) and BglII (7621).

Packaging Plasmids/Helper Virus Constructs (FIG. 5):

(i) pSVC21, which contains the fully infectious proviral clone HXBc2 and an SV40 origin of replication.

(ii) pSVΔP1, a previously described mutant of pSVC21 which has a 19 bp deletion between the major splice donor and gag initiation codon, resulting in impaired viral replication (16).

(iii) pSVΔP2, which has a 36 bp deletion between the splice donor and gag initiation codon of pSVC21. This deletion results in a more severe replication defect.

(iv) pSVΔP1ΔLTR, a non-infectious derivative of pSVΔP1 which was obtained by deleting sequences downstream of the XhoI site (8897). This removes the entire 3' LTR without affecting viral protein synthesis.

(v) pSVΔP1Δenv, a non-infectious mutant of pSVΔP1 lacking a BglII fragment (7041-7621) in the env gene. To produce intact virions, this plasmid was cotransfected with env expression plasmid pLenv, which was derived from pIIIenv3 (14) by removal of the 3'LTR so that the downstream SV40 polyadenylation signal is used.

Procedure:

Vector plasmids containing puro and hygro selectable markers were transfected into the T cell lines Jurkat and Jurkat tat by electroporation. Puromycin was used at 0.5 μg per ml and hygromycin at 500 μg per ml for the selection of vector-containing cells. As Jurkat tat cells already contain a transfected neo gene, the LCNL vector was electroporated into Jurkat cells only. G418 was used at 2 mg per ml for selection. The presence of intact vector in the transfected lines was confirmed by Northern and Southern blotting and by demonstration of CAT activity and drug resistance where appropriate.

Cell lines stably expressing vector RNAs were infected with the HIV-1 isolate HTLV-III$_B$ and progeny virus was harvested 7 days later. In order to assess vector transduction, 1-2 ml of the progeny virus stock was filtered through a 0.45 μm membrane and used to infect $2 \times 10^6$ Jurkat tat cells (Jurkat cells in the case of LCNL). Selection was applied 24 hours later at the concentrations given above and flasks were examined for the presence of live cells after 10–14 days.

Titres of those vectors found to be transducible were calculated using a limiting dilution method as follows: Jurkat tat cells were incubated in flat bottom 96-well plates at $5 \times 10^4$ cells per well, with serial 4-fold dilutions of virus. Six replicate wells were set up at each dilution and selection was applied 24 h after infection. Plates were fed every 5–6 days thereafter by replacing half the medium. Wells were scored for clusters of live cells after three weeks. For vector titration on Hela T4 cells, 90 mm Petri dishes seeded the previous day with $0.5 \times 10^6$ cells were infected with dilutions of virus. Puromycin (0.75 μg per ml) or hygromycin (200 μg per ml) selection was applied 24 h after infection. Colonies were counted ten days later after fixing the plates in 4% formol saline, and staining with 0.1% toluidine blue.

Total cellular RNA was prepared using an acid guanidinium-thiocyanate method (10). The same method was used for virion RNA after first concentrating the virus by polyethylene glycol (PEG) precipitation and high speed centrifugation as follows: stocks of virus stored at $-70°$ C. were thawed and incubated overnight with 0.5 volume of 30% PEG 8000 in 0.4M NaCl. The precipitate was collected by centrifugation at 2000 rpm for 40 minutes at $4°$ C. and resuspended in 0.5 ml of TNE (10 mM Tris.HCl, 150 mM NaCl, 1 mM EDTA pH 7.5). This was layered over an equal volume of TNE containing 20% sucrose and centrifuged at 40,000 rpm ($98,000 \times g$) for 1 hour at $4°$ C. in a Beckman TLA45 rotor. RNA was extracted from the virus pellet with the addition of 10 μg of carrier tRNA. Virion RNA was resuspended in DEPC-treated distilled water, in a volume approximately 1/100th of the initial virus stock.

For Northern blotting, 5 μg of total cellular RNA or 5 μl of virion RNA was run on a formaldehyde 1% agarose gel, transferred onto Zetaprobe membrane (BioRad) in $10 \times$SSC, baked and hybridised overnight at $65°$ C. in 0.25M sodium phosphate pH 7.4, 7% sodium lauryl sulphate (SDS). High specific activity probes were prepared by the random priming method (11) using Klenow polymerase. Membranes were washed 3 times in $3 \times$SSC, 0.1% SDS then 4 times in $0.1 \times$SSC, 0.1% SDS at $65°$ C. prior to autoradiography. EcoR1 fragment 4648-5743 was used as a pol gene probe and LTR sequences were probed with KpnI-HindIII fragment 9015-9616.

For slot blot analysis, virion RNA samples normalised for reverse transcriptase activity and equivalent to approximately 0.5 ml of the unconcentrated virus stock were applied to Zetaprobe membrane under mildly denaturing conditions (ice-cold 10 mM NaOH, 1 mM EDTA). For complete RNA hydrolysis, samples were incubated for 30 minutes in 2M NaOH at $80°$ C. and then applied to the membrane as above. Membranes were baked and hybridised in the same way as Northern blots.

For calculating vector RNA packaging, slot blots of virion DNA were prepared in duplicate and hybridised with vector-specific (puro gene) and virus-specific (pol gene) probes. Bound probe was measured by scintillation counting. To overcome differences in the length and specific activity of the two probes, a reference sample was included in which the stoichiometry of puro and pol hybridising sequences is 1:1. The reference sample consisted of RNA from a puromycin resistant HIV-1 virus containing the puro gene in place of nef. Vector encapsidation, expressed as a percentage of the wild-type helper virus level, was calculated using the formula:

$$100 \times (PUROsample \times POLref)/(PUROref \times POLsample)$$

The above data indicate which vectors are packaged, but do not provide accurate information regarding the packaging efficiencies of different RNAs. Thus, a second calculation was performed. For each of the packageable vectors, a packaging efficiency was calculated by estimating the quantity of full-length vector RNA in the cells and comparing this with the amount subsequently detected in the virions by slot blot analysis. Northern blots of total RNA from HTLV-$III_B$-infected vector lines were hybridised with a vector-specific gene probe (puro) and the relative amounts of full-length vector RNA were estimated by densitometry. Infected cells were used for the analysis so that vector RNA expression was fully transactivated by tat and rev, as for packaging. Hybridisation of selected samples with an LTR probe allowed the levels of vector and HTLC-$III_B$ genomic RNA to be directly compared. The packaging efficiency of the wild-type genome was assigned a value of 1.0 and packaging efficiencies of the full-length vector (FLV) RNAs were calculated using the formula:

$$(FLV\ packaged \times III_B\ genome\ in\ cell)/(FLV\ in\ cell\ III_B\ genome\ packaged)$$

5–10 μg each of vector and packaging plasmids were cotransfected into COS cells using the DEAE dextran technique (17). Virus was harvested after 72 hours, passed through a 0.45 μm filter to remove contaminating cells and then inoculated onto $2 \times 10^6$ Jurkat tat cells. Puromycin selection was applied 24 hours later at 0.5 μg/ml and vector-containing cells were expanded for molecular and virological analysis. RNA was extracted using an acid-guanidinium thiocyanate. Vector transduction efficiency by the various helper plasmids was measured by counting puromycin-resistant Hela cell colonies 10–12 days post-infection after fixing the plates in 5% formol saline and staining with 0.1% Toluidine blue.

High molecular weight DNA prepared from puromycin-selected cells following transfer was examined for the presence of integrated vector and helper virus DNA by Southern blotting. After overnight digestion with Sac1 and electrophoresis in 0.8% agarose, 5 μg DNA samples were transferred onto Zetaprobe membrane (Biorad) by capillary blotting in 0.4M NaOH. High specific activity probes were prepared by the random priming method (12) and overnight hybridisation was performed at $65°$ C. in 0.25M sodium phosphate pH 7.4, 7% sodium lauryl sulphate containing 100 μg/ml sheared salmon sperm DNA.

CAT assays were performed using a standard method (12) using equivalent amounts of protein, as determined by the method of Bradford. Reverse transcriptase activity was measured using $P^{32}$-labelled TTP and the microplate method of Potts (13).

FIG. 4 shows the series of HIV-1 vectors studied. All contain the 5' and 3' LTRs, the 5' untranslated region and the first 43 bp of the gag gene. To investigate transduction of the vectors by a replication-competent helper virus, the vectors were stably transfected into the T cell lines Jurkat and Jurkat tat. These vector lines were then infected with the HIV-1 isolate HTLV-$III_B$ and progeny virus was inoculated on to target cells expressing the HIV receptor CD4. Table 5 summarises the transduction frequencies obtained with two target cell lines for the vectors illustrated in FIG. 4. Helper virus titres in the same stocks were generally in the range $1 \times 10^5 - 5 \times 10^5$ per ml on Jurkat tat cells.

LCNL, LHPL and the LCPL/LPL series of vectors could not be transduced into CD4 expressing cell lines by the helper virus (Table 5). Nor could these vectors be transferred using a transient COS cell-packaging system. The block to vector transduction appears to operate at the level of RNA packaging, as slot blot analysis of RNA extracted from virions after infection of the vector lines with HTLV-III$_B$ showed no detectable vector RNA. The virion RNA samples hybridised strongly to a pol gene probe which detects the helper virus genome and provides a useful gauge of RNA recovery.

To determine whether the failure of these vectors to be encapsidated could be explained by low level expression of the vector RNA, total cellular RNA from these vector lines was analysed by Northern blotting. Full-length vector RNA was detected in all of the vector lines, although the spliced or internally-initiated mRNA was usually more abundant. The relative amounts of full-length vector RNA in the infected vector lines were estimated by densitometry and are shown in Table 6. The quantity of full-length LCPL.PX RNA was very low, possibly as a consequence of cis-acting repressive sequences in the extended gag region. Other non-transferable vectors were more abundant, the full-length RNAs being present at up to 6.8% of the helper virus genomic RNA level. Several packageable vectors were expressed at concentrations lower than this (e.g. HVPM, LRPL); therefore the lack of vector encapsidation cannot be attributed to low abundance of the full length vector RNA. It may be concluded that the packaging signal present in the 5' leader region is not sufficient to allow the encapsidation of HIV-1 based vectors.

The vectors HVP and HVH, which contain gag and protease coding regions, functional tat and rev genes and a partial env gene, were packaged respectively 60% and 19% as efficiently as the wild-type helper virus genome (respective packaging efficiencies 0.33 and 0.22). These vectors could also be transferred to CD4-expressing target cells with titres of approximately $2 \times 10^4$ cfu/ml for HVP and $2 \times 10^3$ cfu/ml for HVH (Table 5). The actual titres may be higher than this, as some cell killing by the HTLV-III$_B$ helper virus does occur, particularly in Jurkat tat cells. These more complex vectors were transcribed at very high levels and gave rise to three spliced RNA species in addition to the full-length RNA. The presence of an abundant packageable RNA such as HVP did not appear to interfere with encapsidation of the wild-type genome or reduce the titre of infectious virus, suggesting that HIV-1 RNA packaging capacity is not saturated during acute infection.

Northern blot analysis of virion RNAs provided direct evidence for the encapsidation of HVP and other vectors. Using an LTR probe, two RNA species were observed. One also hybridised to a pol probe and corresponds to the helper virus genome. The other hybridised to a puro probe and comigrated with the unspliced HVP RNA detectable in the uninfected HVP vector line by a puro probe. The LTR probe also confirmed packaging of HVPM, LGRPL and other packageable vectors. In all these cases, the higher molecular weight species, corresponding to wild-type helper virus RNA, could also be seen. This species is the only one detected in supernatants from non-packageable vector lines. Spliced RNA from HVP can be seen from the HVP vector line probed with puro or with LTR, but no detectable spliced HVP products are encapsidated as shown by the puro probed HVP virion RNA. The same puro probe demonstrates packaged vector RNA from LGRPL, LRPL and other packageable (not shown), however vectors such as LCPL are clearly not detectable. A long exposure of puro probed virion HVP revealed a faint higher molecular weight species corresponding to the size of wild-type virus genome. This is most probably an HVP/HIV recombinant (this species is discussed later). It is clearly present in insufficient quantities to influence the calculations of vector encapsidation efficiency.

The presence of intact HVP vector in the target cells following virus-mediated transfer was confirmed by Northern blot analysis using a puro gene probe. The target cells contained an abundant puro-hybridising RNA identical in length (5.8 kb) to the original vector, as well as spliced vector transcripts. The cells also express a puro-hybridising RNA approximately 9 kb in length which is not present in the original vector line. This RNA appears to be the result of recombination between HVP and the helper virus. The 9 kb recombinant genome was replication-competent and formed the predominant puro-hybridising RNA species in secondary and subsequent rounds of puro gene transduction. The recombinant genome was not observed when the HVP vector was packaged in COS cells.

In the vector HVPM, the gag initiation codon was disrupted by oligonucleotide-directed mutagenesis from GAGATGGGT to GAGTATACT. Both encapsidation level and transduction titre of the mutated vector were reduced 7-fold when compared to the parent HVP vector (Table 5). However an unexpected consequence of the gag mutation was a striking reduction in the steady-state level of vector RNA within the cell and an increase in the proportion of spliced vector transcripts.

Owing to its lower concentration within the cell, the packaging efficiency per molecule of HVPM was greater than that of HVP, although the total amount encapsidated, and hence transduction efficiency, was lower.

The vector HVPΔEC was derived from HVP by removing the gag-pro region so that only the first 43 bp of gag remain. This vector was packaged at 10% of the wild-type level and transduced with a titre of $2 \times 10^3$ cfu/ml, 10-fold lower than that of HVP. The packaging efficiency of HVPΔEC was similar to that of the wild-type genome, however, and its lower encapsidation level can be attributed to reduced RNA abundance (Table 6). Thus, while an intact gag gene appears to enhance high level expression of the RNA, it is clearly not essential for vector packaging. These findings were confirmed by analysis of another vector pair, LRPL and LGRPL (see below).

A further series of plasmids was made to determine the contribution of the env gene to RNA packaging. A factor to be considered was that the structural genes of HIV-1 contain cis-acting repressive sequences (CRS) which inhibit mRNA expression but which can be overcome by the interaction of Rev protein with the cis-acting Rev-responsive element (RRE), located within the env gene. For the efficient expression of CRS-containing RNAs, the RRE must be retained. This is clearly indicated by the vector LGPL, in which all env sequences (including the RRE) have been removed. Although the spliced mRNA encoding puro is expressed, very little unspliced vector RNA is seen in the vector line either before or after infection with HIV-1. This vector was not detectably encapsidated, and was transferred to Jurkat tat cells on rare occasions when a large viral inoculum (up to 5 ml) was used (Table 5). The inefficient encapsidation of LGPL may be due to the extremely low abundance of the unspliced RNA. Alternatively, 3.5 kb LGPL RNA may be too short to be packaged, or may lack a specific 3' packaging signal. To discriminate between these possibilities, three further vectors were analysed.

The vector LGRPL contains a 1.1 kb env fragment spanning the RRE in addition to gag sequences. Consequently, full-length vector RNA is accumulated in the presence of Rev, supplied in this Example by the helper virus. In contrast to LGPL, this RRE-containing vector was encapsidated at high levels and with almost wild-type efficiency, giving titres of $5 \times 10^3$ cfr/ml (Table 6). The LGRPL vector therefore contains all the signals necessary for efficient RNA encapsidation, and 5' env sequences are not required.

To investigate whether env sequences downstream of the RRE contribute to RNA packaging, a HindIII-BamH1 fragment of LGRPL (nucleotides 8141–8475) was removed, creating LGRPLΔBH. The encapsidation level and titre of this vector were reduced approximately 3-fold in comparison to LGRPL. The intracellular concentration of LGRPLΔBH was extremely low, however, so that the packaging efficiency per molecule was significantly greater than that of the wild-type genome (Table 6). This suggests that the missing sequences do not contribute directly to RNA packaging and demonstrates that vector RNAs expressed at less than 1% of the wild-type genomic RNA level can be efficiently transferred.

The LRPL vector differs from LGPPL in lacking all but the first 43 bp of gag. This vector RNA, only 2.6 kb in length, was expressed and packaged at 6% of wild-type levels, demonstrating that gag sequences are not essential for packaging (Table 5).

As vectors similar to LRPL but lacking 3' env sequences (e.g. LCPL.2M) were not encapsidated, it may be postulated that the 1.1 kb env fragment contains an important packaging signal as well as being required for the stable expression of vectors containing cis-acting repressive sequences.

As vectors lacking the gag gene can be transduced with moderate efficiency, this appeared a suitable region for the insertion of foreign genes. However, replacement of the gag-pro region of HVPM with CAT or hygro genes in vectors HVCP and HVHP led to a significant reduction in vector encapsidation. The transduction titres of these vectors, a more sensitive indicator of packaging, were 20 to 40-fold lower than that of HVPM (Table 5). Packaging efficiencies of these vectors were also lower than HVPM, and direct inhibitory effects of the CAT and hygro genes on vector encapsidation have not been excluded (Table 6).

Transduction of these vectors was associated with a very high degree of recombination, as evidenced by Northern blot analysis of RNA from the target cells. Large amounts of the 9 kb recombinant genome were detected but little or none of the original vector. CAT activity was demonstrable in cells following transduction of HVCP, indicating some transfer of the intact vector, and lower levels of CAT activity were occasionally detected following secondary transfer. None of the puromycin-resistant cells arising from HVHP transfer were resistant to hygromycin, indicating that puro gene transfer with this vector is invariably the result of recombination. Northern blotting confirmed this, showing the presence of a 9 kb recombinant RNA but no detectable HVHP vector.

There was clearly no absolute correlation between vector RNA abundance and packaging efficiency: for example, LGRPL was expressed intracellularly at one-third the level of HVP, yet had a packaging efficiency 2 to 3-fold higher (Table 6); similar discrepancies can be seen for HVP and HVPM. Using different vectors in different cell lines also demonstrated that with differing levels of expression there was not a direct correlation with the amount packaged.

Vector packaging was also achieved by transiently co-expressing vector and helper virus plasmids in COS cells. All the plasmids contained an SV40 origin of replication. With this system, it was possible to reduce or eliminate the production of infectious virus by using attenuated or non-infectious packaging constructs. The attenuated viruses, HXBΔP1 and HXBΔP2, contain deletions in the 5' untranslated region which disrupt packaging. The non-infectious provirus HXBΔP1Δenv contains an additional deletion within the env gene and requires a complementary env expression plasmid for the production of intact virions.

The small vector LCPL.PX was not transducible either by infectious or non-infectious helper systems. The same result was obtained with other vectors containing the 5' untranslated region and varying lengths of gag but lacking sequences from the 3' end of the HIV-1 genome. The HVP vector was transduced with moderate efficiency by both infectious and non-infectious packaging constructs. When normalised for reverse transcriptase activity, HVP transduction in this system was 5–10 times less efficient than in T cells. No colonies were obtained using Hela T8 cells, demonstrating the CD4 specificity of the transducing virus. The LGRPL vector was also transferred but approximately 3 times less efficiently than HVP. Transduction of this vector, which does not express tat or rev, was significantly decreased in the absence of infectious virus. The presence of viral proteins in the target cell appears to improve the colony-forming ability of the vector, presumably by enhancing its expression.

The titres of infectious virus in the COS cell supernatants were measured in a $TCID_{50}$ assay Jurkattat cells. The results demonstrate the reduced infectivity of the mutant proviruses HXBΔP1 and HXBΔP2 but also indicate that this level of attenuation is not sufficient to prevent helper virus transmission (Table 7). Infectious virus was also recovered when the HVP vector was cotransfected with the non-infectious provirus HXBΔP1ΔLTR which lacks a 3' LTR. This was not unexpected as only a single recombination event between the vector and packaging virus is required to generate an infectious genome. Infectious virus was eliminated altogether by expressing gag-pol and env proteins from separate plasmids, so that two recombination events would be required to generate an infectious genome. Target cells containing HVP or LGRPL which had been transduced using this "dual plasmid" helper system showed no evidence of reverse transcriptase activity or cytopathic effect during a six week monitoring period. Furthermore, supernatant from these cultures did not transmit puromycin resistance to fresh Jurkat tat cells (secondary transfer) (Table 7).

Northern blot analysis confirmed the presence of the intact vector RNA in the target cells and showed no evidence of infectious virus when the dual plasmid packaging system was used. Hybridisation with a puro gene probe revealed the expected vector transcripts. Using a pol probe (EcoR1 fragment 4648-5743), viral RNA could be demonstrated when infectious helper virus (wild-type HXBc2 and ΔP1) was used, but was not detectable when vector transduction was achieved using the dual plasmid helper system.

Southern blot analysis also confirmed the absence of helper virus DNA when the dual plasmid packaging system was used. Using a Sac1 fragment of LGRPL to probe Sac1-digested genomic DNA, fragments of the expected sizes for HVP (2.20 kb and 3.50 kb) and LGRPL (3.88 kb) were seen. Bands of 3.57 kb and 5.33 kb corresponding to the helper provirus were seen when infectious helper virus was used but not after transfer using the dual plasmid helper system. Where infectious virus was present, an additional fragment was seen; from its length of c.4 kb, it may be deduced that this fragment is the result of recombination between the vector and helper virus. This would produce an extended env+puro fragment of 4.08 kb.

Little or no recombinant RNA (i.e. genome length RNA hybridising with the puro probe) is evident in these cells. Therefore, the recombinant provirus is either not expressed or has been generated subsequent to the selection of vector-containing cells.

TABLE 5

| Vector | CFU/ml[a,b] Jurkat tat | CFU/ml[a,b] Hela T4 | Packaging Efficiency[c] |
|---|---|---|---|
| LCNL/LNL | 0[d] | NT[e] | ND[f] |
| LCPL Series[g] | 0 | 0 | ND |
| LPL series[h] | 0 | 0 | ND |
| LHPL | 0 | 0 | ND |
| LGPL | <1 | 1 | ND |
| HVH | $6.6 \times 10^2$ | $2.3 \times 10^3$ | 19% |
| HVP | $1.7 \times 10^4$ | $1.9 \times 10^4$ | 60% |
| HVPM | $3.1 \times 10^3$ | $4.3 \times 10^3$ | 9% |
| HVPΔEC | $1.8 \times 10^3$ | $3.4 \times 10^3$ | 10% |
| LGRPL | $5.0 \times 10^3$ | $1.1 \times 10^3$ | 25% |
| LGRPLΔBH | $2.1 \times 10^3$ | $3.7 \times 10^3$ | 9.5% |
| LRPL | $1.0 \times 10^3$ | $1.9 \times 10^3$ | 6.4% |
| HVCP | $1.0 \times 10^2$ | $1.0 \times 10^2$ | <1% |
| HVHP | 75 | $1.4 \times 10^2$ | ND |

TABLE 6

| Vector | Relative abundance of full-length RNA[a] | Encapsidation level[b] | Packaging efficiency |
|---|---|---|---|
| HTLV-III$_B$ | 100 | 100 | 1.00 |
| HVP | 180 | 60 | 0.33 |
| HVH | 86 | 19 | 0.22 |
| LGRPL | 30 | 25 | 0.83 |
| HVCP | 10 | 0.4* | 0.04 |
| HVPΔEC | 8.0 | 10 | 1.25 |
| LHPL | 6.8 | ND | |
| LRPL | 6.4 | 5 | 0.88 |
| HVHP | 4.2 | 0.3* | 0.07 |
| HVPM | 4.1 | 9 | 2.20 |
| LCPL.CX | 3.5 | ND | |
| LCPL.HX | 1.2 | ND | |
| LGPL | 1.0 | ND | |
| LGRPLΔBH | 0.9 | 9.5 | 10.6 |
| LCPL.PX | 0.1 | ND | |

TABLE 7

| Vector | Packaging plasmid (s)[a] | Puro® cfu/ml[b] HelaT4 | Puro® cfu/ml[b] HelaT8 | Helper TCID$_{50}$[c] | 2° puro trans- fer |
|---|---|---|---|---|---|
| HVP | (i) pHXBHc2 | 188 | 0 | $4.8 \times 10^3$ | + |
| HVP | (ii) pHXBΔP1 (ψ) | 140 | 0 | $1.5 \times 10^3$ | + |
| HVP | (iii) pHXBΔP2 (ψ) | 195 | 0 | $2.5 \times 10^2$ | + |
| HVP | (iv) pHXBΔP1ΔLTR | 190 | 0 | 10 | + |
| HVP | (v) dual plasmid | 101 | 0 | 0 | − |
| LGRPL | (i) pHXBc2 | 60 | 0 | ND[d] | + |
| LGRPL | (v) dual plasmid | 6 | 0 | ND | − |
| LCPL.PX | (i) pHXBc2 | 0 | 0 | ND | N/A[e] |
| LCPL.PX | (v) dual plasmid | 0 | 0 | ND | N/A |

[a]roman numerals refer to plasmids described above
[b]normalised for RT activity of 1000 cpm/μl
[c]infectious virus titre on Jurkat tat cells
[d]not done
[e]not applicable In conclusion, the gag gene of HIV-1 is not essential for RNA packaging, as illustrated by the successful packaging of the vectors LRPL and HVPΔEC. These gag vectors were expressed at a lower level than their gag counterparts but their packaging efficiencies remained high. A decrease in packaging efficiency was observed when foreign genes were inserted in place of gag, and this may be due to an inhibitory effect of the foreign sequence.

env gene sequences appear to play a more critical role in vector transfer. An important feature of HIV-1 gene expression is the presence of cis-acting repressive sequences (CRS) within the gag and env genes. These sequences inhibit mRNA expression but can be overcome by the interaction of Rev protein with its target RNA sequence, the Rev-responsive element (RRE) located within env. A vector containing gag sequences but lacking the RRE was neither expressed as a full-length RNA nor encapsidated. The inclusion of a 1.1 kb env fragment encompassing the RRE allowed the accumulation of unspliced vector RNA in the presence of Rev and enhanced the transduction of such vectors by a factor of $10^4$. In addition to its influence on the expression of vectors containing cis-acting repressive sequences, this region of env appeared to contain an essential packaging signal and was able to direct the packaging of LRPL, an otherwise minimal vector.

In any practical application of HIV-1 vectors, transmission of the packaging virus must be excluded. Using a transient packaging system in which the vector, an envelope-deficient provirus and a separate env-expression plasmid were co-transfected into COS cells, Example 2 shows that virus-free transfer of HIV-1 vectors is both feasible and CD4-specific. Two recombination events would be required to produce an infectious genome and in no instance has this been observed. With optimal transfection conditions, vector titres were 100-fold lower in the COS cell system than in the T cell (vector line) system. Cis-sequences required for vector packaging appeared to be the same in both cell types and in neither system could transfer of vectors lacking 3' env sequences be detected.

Several laboratories have reported the successful encapsidation or transduction of RNAs which contain only the LTRs, the 5' leader region and, in some cases, part of gag. The findings herein are in contrast to these published reports, e.g. in WO-A-9119798, but the vector transfer data presented here are supported by extensive RNA analysis and careful measurements of RNA encapsidation. The vector titres correlate remarkably well with the encapsidation level, but neither packaging nor transfer of vectors lacking the 3' region of env could be demonstrated.

The discrepancy between these results and those reported in WO-9119798 may relate to the experimental systems used. All previously published studies have used transient plasmid expression systems to analyse RNA encapsidation whereas, in this study, HIV-1 vectors were stably expressed in T cell lines and packaged by a replication-competent helper virus in the course of a natural infection. This system has the advantages of simulating the expression of a stably integrated provirus and rigorously excluding any possibility of DNA-mediated gene transfer (for example as residual plasmid DNA coating the virus particles).

The packaging of HIV-1 based vectors is chiefly determined by the presence of cis-acting signals, but vector RNA abundance and the presence of 5' heterologous sequences also appear to influence the amount packaged. Based on the comprehensive study described here, the 5' leader region is apparently not sufficient for the packaging of HIV-1 vectors, and 3' env sequences contain an important packaging signal. While 5' leader sequences downstream of the HIV-1 splice donor site are apparently not sufficient for RNA packaging, these sequences must play a definitive role in the selection of RNAs for encapsidation, as the env mRNA of HIV-1 is not detectably encapsidated.

The identification of HIV-1 packaging signals allows the exploitation of HIV as a means of gene transfer. HIV-1 retroviral vectors carrying antiviral genes represent a potentially useful approach to AIDS therapy, and offer scope for the specific targeting of such genes to CD4-expressing cells. The ability of wild-type virus to encapsidate RNA from stably integrated vectors as demonstrated here may be useful in patients infected with HIV where packageable antiviral constructs introduced into a population of the individuals CD4+ cells might be disseminated by the patients' own virus. A fuller understanding of RNA encapsidation and virus assembly may also identify new targets for antiviral therapy.

We claim:

1. A vector comprising a polynucleotide sequence which encodes MPMV (Mason-Pfizer Monkey Virus) proteins, said polynucleotide sequence comprising an MPMV leader sequence which is a deletion mutant of SEQ ID NO. 2, wherein said MPMV leader sequence has an effective deletion of nucleotides which results in MPMV RNA transcribed from said vector being packaging defective, said deletion occurring between the MPMV primer-binding site at nucleotides 348–365 of SEQ ID NO. 2 and the MPMV 5' major splice donor at nucleotides 475–480 of SEQ ID NO. 2.

2. The vector according to claim 1, wherein the deletion comprises bases 28 to 50 of SEQ ID NO. 1.

3. The vector according to claim 1, wherein the deletion comprises bases 51 to 112 of SEQ ID NO. 1.

4. The vector according to claim 1, wherein the deletion comprises SEQ ID NO. 1.

5. The vector according to claim 1, which contains sequences corresponding to a promoter region in the MPMV genome or another genome's polyadenylation sequence but does not contain sequences corresponding to a MPMV long terminal repeat sequence.

6. The vector according to claim 1, which permits expression of MPMV proteins upstream of env or of the remaining proteins, and which optionally also includes a marker.

7. A vector comprising nucleotides corresponding to the packaging nucleotides of MPMV, a heterologous gene and, flanking the packaging nucleotides and the heterologous gene, sequences corresponding to those within and near the MPMV long terminal repeat sequence sufficient for packaging, reverse transcription and integration of the vector into target cells and expression of the heterologous gene, wherein the packaging nucleotides are selected from the group consisting of the nucleotides between the MPMV primer-binding site at nucleotides 348–365 of SEQ ID NO. 2 and the MPMV 5' major splice donor at nucleotides 475–480 of SEQ ID NO. 2, nucleotides 28 to 50 of SEQ ID NO. 1, nucleotides 51 to 112 of SEQ ID NO. 1, and nucleotides 1 to 121 of SEQ ID NO. 1.

8. The vector according to claim 7, which comprises the first 500 bp of the MPMV gag gene.

9. The vector according to claim 7, wherein nucleotides corresponding to the nucleotide sequence numbered 481–493 between the MPMV 5' major splice donor and the MPMV initiation codon of SEQ ID NO. 2 are deleted.

10. A method of gene transfer in vitro, which comprises transfecting virion-producing cells with one or more packaging-deficient MPMV or HIV vectors and a vector according to claim 7.

11. The method according to claim 10, which additionally comprises culturing the cells and contacting the resultant virions with mammalian cells.

12. The vector, according to claim 7, which comprises a MPMV or HIV LTR sequence as a promoter for the heterologous gene.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 121 bases
        ( B ) TYPE: nucleic acid
        ( C ) STRANDEDNESS: single
        ( D ) TOPOLOGY: linear     ( i i ) MOLECULE TYPE: DNA (synthetic)

( x i ) SEQUENCE DESCRIPTION: SEQ ID NO:1:

```
GGCGCCCAAC  GTGGGGCTGG  ATACGAGGGA  ATTTCGTGAG  GAAGACGACG  CGTTCGCCGG       60
CCGGCGATTA  AAAGTGAAAG  TAAACTCTCT  TGGCCGCCGC  GGGAACCTGC  CGCGTTGGAC      120
C                                                                          121
```

( 2 ) INFORMATION FOR SEQ ID NO:2:

( i ) SEQUENCE CHARACTERISTICS:
        ( A ) LENGTH: 499 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:2:

```
TGTCCGGAGC  CGTGCTGGCC  GGATGTGTCT  TGGCCTCTGT  TTGCTCTAGC  TCCATGTTAT       60
GAATTTAACA  TGGCGTATTT  CCTGGTTCTT  CTCCGTCTTA  CTTTCCCGCC  GGCGCGAATG      120
TTTCCCGCTC  TTGGGCTTAG  GTGGCTTTCC  TTGCTCTGCT  ACTGAGCATG  CGCCCAGTAT      180
CTTTCCCCTC  CCACTTGCTG  CCTGTGTATA  TAAGGCAACA  CATTGCCACC  ATTAAATGAG      240
ACTTGATCAG  AACACTGTCT  TGTCTCCATT  TCTTGTGTCT  CTTGTTCCCT  TCAATTCCCA      300
CTCCCTCCTC  CAGGTTCCTA  CTGTTGATCC  CGCGGGTCGG  GACAGTTGGC  GCCCAACGTG      360
GGGCTGGATA  CGAGGGAATT  TCGTGAGGAA  GACGACGCGT  TCGCCGGCCG  GCGATTAAAA      420
GTGAAAGTAA  ACTCTCTTGG  CCGCCGCGGG  AACCTGCCGC  GTTGGACCTG  AAAGTAAGTG      480
TTGCGCTCGG  ATATGGGGC                                                      499
```